United States Patent [19]
Nishiyama et al.

[11] Patent Number: 5,936,104
[45] Date of Patent: Aug. 10, 1999

[54] PROCESS FOR PRODUCING 1,2-EPOXY-3-AMINO-4-PHENYLBUTANE DERIVATIVES

[75] Inventors: Akira Nishiyama, Kobe; Tadashi Sugawa, Akashi; Hajime Manabe, Takasago; Kenji Inoue, Kakogawa; Noritaka Yoshida, Matsubana, all of Japan

[73] Assignee: Kaneka Corporation, Osaka, Japan

[21] Appl. No.: 08/907,461

[22] Filed: Aug. 8, 1997

Related U.S. Application Data

[63] Continuation-in-part of application No. 08/722,102, filed as application No. PCT/JP96/00212, Feb. 2, 1996.

[30] Foreign Application Priority Data

Feb. 3, 1995 [JP] Japan .................................... 7-039266
Sep. 26, 1995 [JP] Japan .................................... 7-273547

[51] Int. Cl.⁶ ................................................. C07D 303/38
[52] U.S. Cl. .......................................................... 549/521
[58] Field of Search ............................................. 549/521

[56] References Cited

U.S. PATENT DOCUMENTS 5,550,291 8/1996 Beaulieu et al. ........................ 564/357
5,610,190 3/1997 Talley et al. ............................. 514/595

FOREIGN PATENT DOCUMENTS

| 4 442 754 A2 | 8/1991 | European Pat. Off. ........ C07C 69/63 |
| 0 580 402 A2 | 1/1994 | European Pat. Off. ...... C07C 271/20 |
| 0 580 402 A3 | 1/1994 | European Pat. Off. ...... C07C 271/20 |
| 0 719 769 A2 | 7/1996 | European Pat. Off. ...... C07D 303/36 |
| 0 719 769 A3 | 7/1996 | European Pat. Off. ...... C07D 303/36 |
| 1 233 678 | 5/1971 | United Kingdom ............ C07C 29/00 |

*Primary Examiner*—Bernard Dentz
*Attorney, Agent, or Firm*—Pollock, Vande Sande & Amernick

[57] ABSTRACT

The present invention provides a process for producing 1,2-epoxy-3-amino-4-phenylbutane derivatives which comprises treating a 1-halo-2-hydroxy-3-amino-4-phenylbutane derivative with a base in an aprotic polar organic solvent or a mixed solvent composed of an aprotic polar organic solvent and water and then causing the resulting epoxide to crystallize out from a mixed solvent composed of an aprotic polar organic solvent and water.

20 Claims, No Drawings

PROCESS FOR PRODUCING 1,2-EPOXY-3-AMINO-4-PHENYLBUTANE DERIVATIVES

CROSS-REFERENCE TO RELATED APPLICATIONS

This is a Continuation-In-Part of applicant's copending U.S. patent application Ser. No. 08/772,102, (U.S. national phase of PCT/JP96/00212 filed Feb. 2, 1996) entitled "PROCESSES FOR PRODUCING α-HALOKETONES, α-HALOHYDRINS AND EPOXIDES" entire disclosure of which is incorporated herein by reference.

FIELD OF THE INVENTION

The present invention relates to a process for producing 1,2-epoxy-3-amino-4-phenylbutane derivatives of the formula (1)

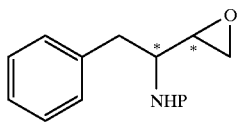

(1)

(wherein P is an amino-protecting group of the urethane type and the configurations at positions 2 and 3 are collectively 2S,3S or 2R,3R). The 1,2-epoxy-3-amino-4-phenylbutane derivatives (1), in particular (2S,3S)-1,2-epoxy-3-amino-4-phenylbutane derivatives of the formula (1a)

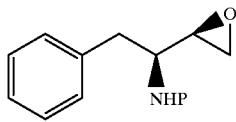

(1a)

(wherein P is as defined above), are very useful as intermediates for the production of various HIV (human immunodeficiency virus) protease inhibitors, as described in, for example, Japanese Kokai Publication Hei-08-109131.

BACKGROUND OF THE INVENTION

Prior art processes for the production of 1,2-epoxy-3-amino-4-phenylbutane derivatives (1) (hereinafter also referred to as "epoxides (1)"), in particular (2S,3S)-1,2-epoxy-3-amino-4-phenylbutane derivatives (1a) (hereinafter also referred to as "epoxides (1a)"), which comprise subjecting (2S,3S)1-halo-2-hydroxy-3-amino-4-phenylbutane derivatives (hereinafter also referred to as "halohydrins (2a)") of the formula (2a)

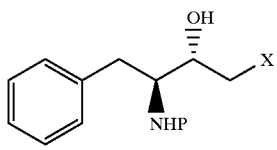

(2a)

(wherein X is a halogen atom and P is as defined above), to ring closure under basic or alkaline conditions, are described, for example, in WO 96/17821, Japanese Kokai Publication Hei-08-109131, Japanese Kokai Publication Sho-62-126158 and Journal of Organic Chemistry, volume 59, pages 3656 ff (1994).

According to WO 96/17821, for instance, (2S,3S)-1-chloro2-hydroxy-3-N-(tert-butoxycarbonyl)amino-4-phenylbutane is converted to (2S,3S)-1,2-epoxy-3-N-(tert-butoxycarbonyl) amino-4-phenylbutane by treatment in THF (tetrahydrofuran) with a solution of KOH in methanol. The reaction mixture is poured into water, whereby (2S,3S)-1,2-epoxy-3-N-(tert-butoxycarbonyl)amino-4-phenylbutane is recovered as crystals (yield 96%, purity 90%).

According to Japanese Kokai Publication Hei-08-109131, (2S,3S)-1,2-epoxy-3-N-(tert-butoxycarbonyl)amino-4-phenylbutane is synthesized by adding a solution of KOH in ethanol to a suspension of (2S,3S)-1-chloro-2-hydroxy-3-N-(tert-butoxycarbonyl)amino-4-phenylbutane in ethanol, followed by 1 hour of stirring at room temperature. Thereafter, the ethanol is distilled off from the reaction mixture under reduced pressure, the residue is partitioned between ethyl acetate and water. The organic layer is washed with an aqueous solution of ammonium chloride, water and an aqueous solution of sodium chloride, dried over magnesium sulfate and concentrated. The solid obtained is dissolved in ethyl acetate, hexane is then added and the mixture is cooled to −40° C. By this recrystallization procedure, (2S,3S)-1,2-epoxy-3-N-(tert-butoxycarbonyl)amino-4-phenylbutane is isolated as crystals (yield 84%, purity 99.1%).

According to Japanese Kokai Publication Sho-62-126158, (2S,3S)-1,2-epoxy-3-N-(tert-butoxycarbonyl) amino-4-phenylbutane is synthesized by adding sodium hydride to a solution of (2S,3S)-1-chloro-2-hydroxy-3-N-(tert-butoxycarbonyl)amino-4-phenylbutane in THF, followed by overnight stirring. Thereafter, the reaction mixture is filtered, the filtrate is concentrated, the oily concentrate is dissolved in ethyl acetate, and the organic layer is washed in sequence with water, aqueous sodium hydrogen carbonate and aqueous potassium hydrogen sulfate, dried over sodium sulfate and then concentrated. The solid obtained is purified by column chromatography to give (2S,3S)-1,2-epoxy-3-N-(tert-butoxycarbonyl)amino-4-phenylbutane in 68% yield.

According to Journal of Organic Chemistry, volume 59, pages 3656 ff (1994), (2S,3S)-1,2-epoxy-3-N-(tert-butoxycarbonyl)amino-4-phenylbutane is synthesized by adding a solution of potassium hydroxide in methanol to a suspension of (2S,3S)1-bromo-2-hydroxy-3-N-(tert-butoxycarbonyl)amino-4-phenylbutane in methanol, followed by 3 hours of stirring at room temperature. Thereafter, the ethanol is distilled off from the reaction mixture, and the residue is partitioned between methylene chloride and water. The organic phase is dried over sodium sulfate and, after removal of the sodium sulfate, concentrated to dryness (yield 100%). The solid obtained is recrystallized from hexane to give analytically pure (2S,3S)-1,2-epoxy-3-N-(tert-butoxycarbonyl)amino-4-phenylbutane.

The starting halohydrins (2a), such as (2S,3S)-1-chloro2-hydroxy-3-N-(tert-butoxycarbonyl)amino-4-phenylbutane and (2S,3S)-1-bromo-2-hydroxy-3-N-(tert-butoxycarbonyl) amino-4-phenylbutane can be prepared in a crystalline or solution form by the methods described in WO 96/23756, WO 96/17821, Japanese Kokai Publication Hei-08-109131, Japanese Kokai Publication Sho-62-126158 and Journal of Organic Chemistry, volume 59, pages 3656 ff (1994), for instance. According to said methods, the halohydrins (2a) are invariably synthesized starting with the corresponding L-phenylalanine derivatives.

(2R,3R)-1,2-Epoxy-3-amino-4-phenylbutane derivatives (hereinafter also referred to as "epoxides (1b)") of the formula (1b)

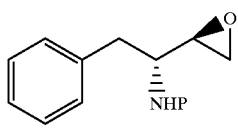

(1b)

(wherein P is as defined above), which are enantiomers to epoxides (1a), can be synthesized by quite the same methods as those described in the above-cited references via the corresponding (2R,3R)1-halo-2-hydroxy-3-amino-4-phenylbutane derivatives (hereinafter also referred to as "halohydrins (2b)") of the formula (2b)

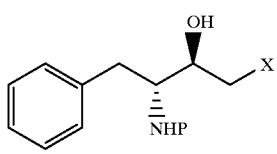

(2b)

(wherein X and P are as defined above), starting with the corresponding D-phenylalanine derivatives, which are enantiomers to the L-phenylalanine derivatives.

Although the description which follows is limited to epoxides (1a), the same applies to epoxides (1b), which are enantiomers to (1a), provided that enanthiomers to those compounds with specified configurations which are mentioned in the following description are used.

The epoxides (1a) obtained in the above manner have a problem in that they tend to contain various impurities resulting from various decomposition and side reactions in the production process steps. In addition, the epoxides (1a) may be contaminated by some or other impurity contained in the starting halohydrins (2a) and/or a conversion product derived therefrom under the reaction conditions. Particular mention should be made of three kinds of impurity among most possibly coexisting impurities. In the following, the three impurities are described one by one (see the schematic illustration shown below).

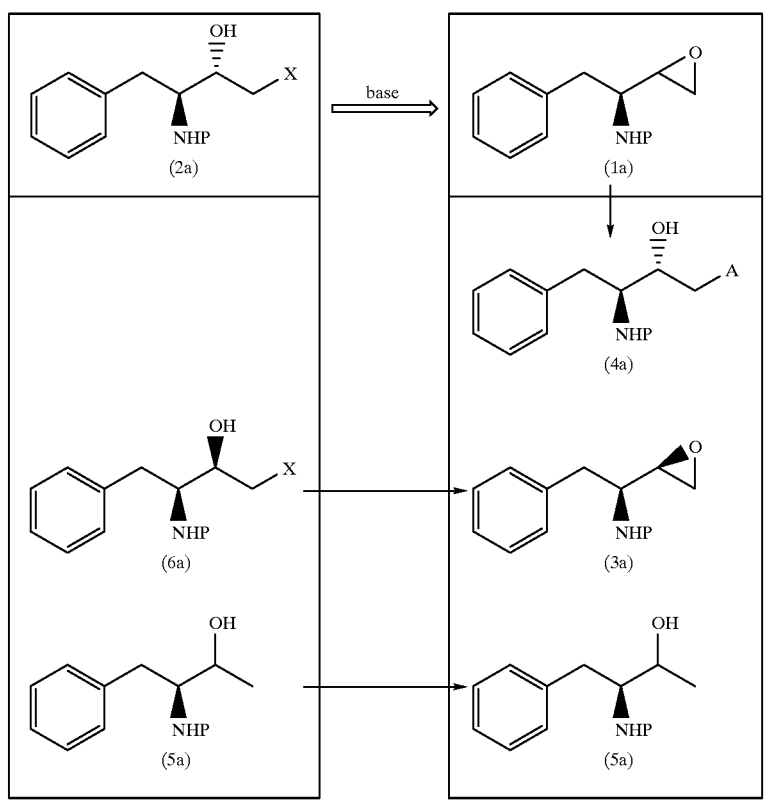

The first kind of impurity comprises threo-(2R,3R)-1,2-epoxy-3-amino-4-phenylbutane derivatives (hereinafter also referred to as "threo-epoxides (3a)") of the formula (3a)

(3a)

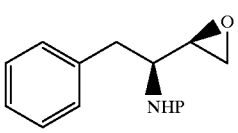

(wherein P is as defined above). The threo-epoxides (3a) occurring as impurities in the epoxides (1a) are produced by cyclization of threo-1-halo-2-hydroxy-3-amino-4-phenylbutane derivatives (hereinafter also referred to as "threo-halohydrins (6a)") of the formula (6a)

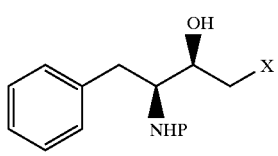

(6a)

(wherein X and P are as defined above and the configurations at positions 2 and 3 are collectively 2R,3S), which occur in the starting halohydrins (2a), under the reaction conditions employed for the cyclization of halohydrins (2a).

The occurrence of threo-halohydrins (6a) in halohydrins (2a) results from the selectivity of the reaction determining the configurations at positions 2 and 3 in the synthesis of halohydrins (2a). Therefore, unless the synthesis of halohydrins (2a) proceeds with 100% selectivity or unless the byproducts threo-halohydrins (6a) are completely removed, the formation of threo-epoxides (3a) as byproducts cannot be avoided. No reactions are known to proceed with 100% selectivity, however. Thus, generally, it is very difficult to obtain halohydrins (2a) free of threo-halohydrins (6a). Purification by column chromatography or repetition of effective crystallization or recrystallization is indispensable and the employment of such procedures unfavorable to commercial scale production is unavoidable. Namely, the prior art technologies teaching the processes for producing halohydrins (2a) [wO 96/23756; WO 96/17821; Japanese Kokai Publication Hei-08-109131; Japanese Kokai Publication Sho-62-126158; Journal of Organic Chemistry, volume 59, pages 3656 ff (1994)] each generally allows contamination of the starting halohydrins (2a) with the impurities threo-halohydrins (6a) unless such troublesome purification methods as mentioned above are used. When such contaminated halohydrins (2a) are used, the prior art technologies mentioned hereinabove (WO 96/17821; Japanese Kokai Publication Hei-08-109131; Japanese Kokai Publication Sho-626-126158) invariably and inevitably make it necessary to remove the threo-epoxides (3a).

As the second kind of impurity, there may be mentioned (2S,3S)1-alkoxy-2-hydroxy-3-amino-4-phenylbutane derivatives (hereinafter also referred to as "epoxy ring opening products (4a)") of the formula (4a)

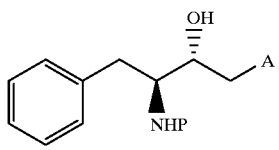

(4a)

(wherein P is as defined above and A is an alkoxy group). In carrying out the cyclization of halohydrins (2a) to epoxides (1a), an alcoholic alkali metal hydroxide or an alkali metal alkoxide is used as a base in most cases. An investigation made by the present inventors revealed that when such base is used for the cyclization reaction of halohydrins (2a) to epoxides (1a), the epoxides (1a) formed are decomposed by the alcohol or alkoxide occurring in the reaction system and the epoxy ring opening products (4a) as byproducts are formed in considerable amounts. This formation of epoxy ring opening products (4a) as byproducts is the main cause of decreased yields. In particular, it was found that when the epoxides (1a) are synthesized by the processes of WO 96/17821, Japanese Kokai Publication Hei-08-109131 and Journal of Organic Chemistry, volume 59, pp. 3656 ff (1994), it is very difficult to suppress the formation of epoxy ring opening products (4a) as byproducts, the reaction can never proceed quantitatively and therefore it is very important to remove them for the purification of (1a).

As the third kind of impurity, there may be mentioned (3S)-2-hydroxy-3-amino-4-phenylbutane derivatives (hereinafter also referred to as "dehalogenation products (5a)") of the formula (5a)

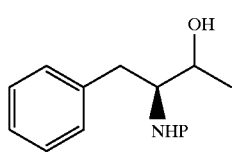

(5a)

(wherein P is as defined above).

The dehalogenation products (5a) are compounds with a structure such that the halogen atom in halohydrins (2a) has been replaced by a hydrogen atom. Why said dehalogenation products (5a) are formed as byproducts is not clear. An investigation by the present inventors, however, revealed that the dehalogenation products (5a) originally occurring in the starting halohydrins (2a) remain unchanged under the cyclization reaction conditions and are brought, as they are and as impurities, into the epoxides (1a). An investigation by the present inventors further revealed that, among the prior art technologies for the production of halohydrins (2a), at least the technology of WO 96/23756 allows the formation of said dehalogenation products.

To sum up, the formation of such various impurities such as threo-epoxides (3a), epoxy ring opening products (4a) and dehalogenation products (5a) and the difficulty of removing them are the major causes of the difficulty in producing high-quality epoxides (1a). As is generally known in the art, related impurities, namely impurities similar in structure to desired products, are difficult to remove for purifying said desired products. For obtaining high-quality desired products, a production process involving a reaction scheme by which byproduct formation can be prevented as far as possible as well as a purification method enabling a high level elimination of impurities is required.

The prior art processes have not only the above-mentioned problems from the quality viewpoint but also other various problems from the method of obtaining viewpoint, for example from the viewpoint of workability or productivity.

Thus, for example, the process of WO 96/17821 is a recipe involving the formation of epoxy ring opening products (4a) as byproducts; it is difficult to obtain high-quality epoxides (1a) and only low purity crystals with at most 90% purity can be obtained. As a result of an investigation by the present inventors, it was found that said process additionally has productivity problems; for example the separation of crystals by filtration is not easy.

The process of Japanese Kokai Publication Hei-08-109131 is also a recipe according to which the formation of epoxy ring opening products (4a) as byproducts is very difficult to suppress, Said process has many problems as regards the method of product recovery as well. For example, two concentration procedures are required, an undesirable organic solvent is used in large amounts, and a cryostat is required to maintain a temperature of −40° C. For these and other reasons, said process is a troublesome, expensive and time-consuming one. Furthermore, the yield is around 84%, hence quite unsatisfactory.

The process of Japanese Kokai Publication Sho-62-126158, too, has too many drawbacks to be put to practical use on a commercial scale; for example, sodium hydride, which is hazardous, is used, two concentration procedures are required, an undesirable organic solvent is used in large amounts, and purification by column chromatography is required. Furthermore, the yield is as low as 68%.

The process of Journal of Organic Chemistry (volume 59, pages 3656 ff, 1994) is also a process essentially involving the formation of epoxy ring opening products (4a) as byproducts and has too many drawbacks to be put to practical use on a commercial scale; for example, two concentration procedures are required, an undesirable organic solvent is used in large amounts, and recrystallization is required.

As mentioned above, the prior art processes each has various drawbacks in employing them in the production on a commercial scale, such as the use of an undesirable organic solvent in large amounts, the complicatedness of process steps, time consumption resulting therefrom, the increases in number and capacity of (expensive) production apparatus and the decreases in yield.

HIV protease inhibitors currently attracting much attention are drugs required to be taken at high doses and therefore it is desired that measures be taken to avoid adverse reactions due to trace impurities and achieve mass production at a cost as low as possible. In such circumstances, it is of particular significance to develop a process for producing high quality epoxides (1a), which are intermediates for the production of HIV protease inhibitors, on a commercial scale with high productivity.

SUMMARY OF THE INVENTION

In view of such present situation, the present inventors made intensive investigations in an attempt to develop a process for producing high quality epoxides (1a) on a commercial scale in a simple and efficient manner with very high productivity and, as a result, found that when halohydrins (2a) are treated with a base in an aprotic polar organic solvent or in a mixed solvent composed of an aprotic polar organic solvent and water, the desired reaction can proceed to give epoxides (1a) in high yields while the formation of the byproducts epoxy ring opening products (4a) is entirely prevented. Furthermore, as a result of an intensive investigation regarding the removal of contaminant impurities in epoxides (1a), in particular threo-epoxides (3a) and dehalogenation products (5a), they found that when the epoxides (1a) are crystallized out from a mixed solvent composed of an aprotic polar organic solvent and water, highly pure epoxides (1a) having good crystalline characteristics can be obtained as crystals in a very simple and easy manner. Based on such and other findings, the present invention has now been completed.

Thus the present invention is concerned with a process for producing 1,2-epoxy-3-amino-4-phenylbutane derivatives of the formula (1)

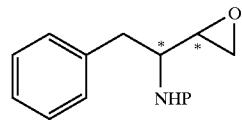

(1)

(wherein P is an amino-protecting group of the urethane type and the configurations at positions 2 and 3 are collectively 2S,3S or 2R,3R), which comprises treating a 1-halo-2-hydroxy3-amino-4-phenylbutane derivative of the formula (2)

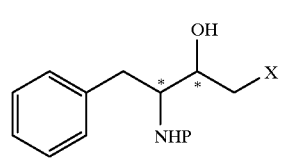

(2)

(wherein X is a halogen atom, P is as defined above and the configurations at positions 2 and 3 are such that when, in formula (1), the configurations at positions 2 and 3 are collectively 2S,3S, they are collectively 2S,3S and, when the configurations in formula (1) are collectively 2R,3R, they are collectively 2R,3R), with a base in an aprotic polar organic solvent or a mixed solvent composed of an aprotic polar organic solvent and water and then causing the resulting 1,2-epoxy-3-amino-4-phenylbutane derivative (1) to crystallize out from a mixed solvent composed of an aprotic polar organic solvent and water.

The present invention is further concerned with a method of recovering 1,2-epoxy-3-amino-4-phenylbutane derivatives of the formula (1)

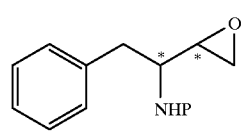

(1)

(wherein P is an amino-protecting group of the urethane type and the configurations at positions 2 and 3 are collectively 2S,3S or 2R,3R), which comprises causing the 1,2-epoxy-3-amino-4-phenylbutane derivatives (1) to crystallize out from a mixed solvent composed of an aprotic polar organic solvent and water.

DETAILED DESCRIPTION OF THE INVENTION

The 1,2-epoxy-3-amino-4-phenylbutane derivatives (1) include two forms, namely (2S,3S)-1,2-epoxy-3-amino-4-phenylbutane derivatives of the formula (1a)

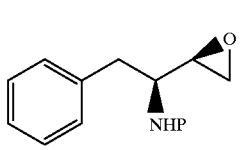

(1a)

(wherein P is as defined above), and (2R,3R)-1,2-epoxy-3-amino-4-phenylbutane derivatives of the formula (1b)

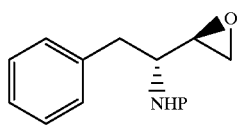

(1b)

(wherein P is as defined above). In the description that follows, however, mention is made only of the epoxides (1a). As regards the epoxides (1b), which are enantiomers to the epoxides (1a), there is no difference from the case of epoxides (1a), as already mentioned hereinabove, provided that enantiomers to those compounds with specified configurations which are mentioned in the following description are used.

In the practice of the present invention, the group P bound to the amino group of the (2S,3S)-1,2-epoxy-3-amino-4-phenylbutane derivatives of formula (1a) or the (2S,3S)-1-halo-2-hydroxy-3-amino-4-phenylbutane derivatives of formula (2a) represents an amino-protecting group. This amino-protecting group is a group effective in protecting the amino group and generally includes those protective groups described in monographs on this field, for example "Protective Groups in Organic Synthesis, second edition (John Wiley & Sons, 1991). Among these protective groups, protective groups of the urethane type (also referred to as carbamate type protective groups) are preferred. More specifically, mention may be made of benzyloxycarbonyl, methoxycarbonyl, ethoxycarbonyl, tert-butoxycarbonyl and the like and preferred species are benzyloxycarbonyl, methoxycarbonyl and tert-butoxycarbonyl.

The substituent X in the (2S,3S)-1-halo-2-hydroxy-3-amino-4-phenylbutane derivatives of formula (2a) is a halogen atom. From the ease of substrate synthesis viewpoint, a chlorine or bromine atom is preferred and a chlorine atom is most preferred.

In accordance with the present invention, a halohydrin (2a) is first treated with a base in an aprotic polar organic solvent or a mixed solvent composed of an aprotic polar organic solvent and water for the formation of the corresponding epoxide (1a).

The aprotic polar organic solvent to be used in the practice of the present invention is one of those showing no nucleophilicity for epoxides (1a) even under cyclization reaction conditions. As examples, there may be mentioned those solvents highly miscible with water, for example THF, acetone, acetonitrile, dimethylformamide, dimethyl sulfoxide, dioxane, dimethoxyethane, diethoxyethane and the like. Among these, acetone, acetonitrile, THF and the like are preferred, and acetone is most preferred, from the ease of handling viewpoint. Such solvents as mentioned above may be used alone or two or more of them may be used in the form of a mixture. The term "organic solvents highly miscible with water" as used herein generally means those solvents which when mixed with the same volume of pure water with gentle stirring at a temperature of 20° C. and one atmospheric pressure, give mixtures remaining homogeneous in appearance even after cessation of undulation. The fact that when an alcohol, which is a protic polar organic solvent, is used as a polar organic solvent, epoxy ring opening products (4a), which are difficult to eliminate, are formed means that particular attention should be paid in solvent selection.

In cases where a mixed solvent composed of an aprotic polar organic solvent and water is used as the reaction solvent, the ratio water/aprotic polar organic solvent is not critical but, when expressed in terms of volume ratio, it is, for example, not more than 10, generally not more than 5, preferably not more than 1. The ratio between water and the aprotic polar organic solvent which is preferred may vary depending on various factors, for example the aprotic polar organic solvent species, the basic strength and the reaction temperature, hence cannot be specified in all cases. However, said ratio can be easily determined by a simple experiment.

The base to be used in the practice of the present invention is not limited to any particular species but includes alkali metal hydroxides and carbonates and alkaline earth metal hydroxides and carbonates. When necessary, two or more of these may be used in combination. Among such bases, alkali metal hydroxides and alkaline earth metal hydroxides are preferred from the rate of reaction viewpoint and alkali metal hydroxides such as lithium hydroxide, sodium hydroxide and potassium hydroxide are more preferred because of their being inexpensive and easy to handle and because of ease of waste water treatment. These bases may of course be used either in a solid form or in an aqueous solution form. From the ease of handling viewpoint, among others, they are preferably used in an aqueous solution form. Generally, 1 to 20 N aqueous alkali metal hydroxide solutions, for instance, are conveniently used. The base is used at least in an approximately stoichiometric amount. However, the use in excessively large amounts is uneconomical. Hence, the base is generally used in an amount of about 1 to 10 equivalents, preferably about 1 to 3 equivalents.

Although the reaction temperature is not critical, the reaction can suitably be carried out at a low temperature at which the reaction mixture will not solidify to about 60° C. At about 20° C. to about 40° C., the reaction can be generally driven to completion in several hours.

The substrate concentration is not critical but the reaction can generally be carried out at a high halohydrin (2a) concentration in the reaction solvent of not less than about 10% (w/v).

The recovery method of the present invention will now be explained.

The thus-formed epoxides (1a) are recovered as crystals by crystallizing out from a mixed solvent composed of an aprotic polar organic solvent and water.

The aprotic polar organic solvent to be used in crystallization is as mentioned hereinabove. This aprotic polar organic solvent may be the aprotic polar organic solvent already existing in the reaction mixture or a newly added one. It is convenient, however, to use the existing one as it is.

The crystallization can be effected, for example, by cooling to thereby reduce the solubility (crystallization upon cooling), concentrating to thereby reduce the amount remaining dissolved (crystallization upon concentration), increasing the proportion of water to thereby reduce the solubility, or a combination of these. In cases where the reaction solvent is an aprotic polar organic solvent, crystals can be recovered by adding water to the reaction mixture, if necessary followed by cooling. When the reaction solvent is a mixed solvent composed of an aprotic polar organic solvent and water, crystals can be recovered by cooling the reaction mixture with or without further addition of water. In cases where the reaction solvent is a mixed solvent composed of an aprotic polar organic solvent and water, it is also possible to effect the reaction and crystallization by selecting conditions favorable to the reaction and crystallization to thereby cause the epoxides (1a) formed to crystallize out successively with the progress of the reaction.

When necessary, the base component remaining in the reaction mixture may be removed or annihilated prior to the step of crystallization.

The base component can be annihilated by neutralizing with an acid.

The acid to be used for neutralization is not limited to any particular species but includes mineral acids such as hydrochloric acid, sulfuric acid and phosphoric acid, organic acids such as acetic acid and formic acid, and salts thereof. When necessary, two or more of these may be used combinedly. Among these acids, mineral acids such as hydrochloric acid and sulfuric acid are preferred because of their being inexpensive and easy to handle and because of ease of waste water treatment, among others. By selecting a favorable combination of base and acid in the practice of the present invention, an inorganic salt which facilitates waste water treatment is formed upon neutralization.

Another method of removing the base component is applicable to those cases in which the reaction mixture separates into two layers (organic layer and aqueous layer). In such cases, the base component can be removed by separating the base component-containing aqueous layer from the system.

In cases where the base component precipitates out, a further method of removing the base component is applicable which consists in removing the base component by filtration.

The water/aprotic polar organic solvent ratio in the step of crystallization is not critical but, when expressed in terms of volume ratio at the end of the crystallization process, it may suitably be, for example, not less than about 0.1, preferably not less than about 0.3, more preferably not less than about 1. The water/aprotic polar organic solvent ratio which is preferred may vary depending on various factors, for example the aprotic polar organic solvent employed and the crystallization temperature, hence cannot be specified in all cases but can be easily determined by a simple experiment.

Although the crystallization temperature is not critical, the crystallization can suitably be effected at a low temperature at which the mixture will not solidify to about 60° C. The yield may be increased by finally cooling the mixture but, when the crystallization step is conducted at a temperature of about 0° C. to 30° C., high yields can advantageously be obtained without using any particular cryogenic apparatus.

The intensity of stirring in the crystallization step is not critical. For obtaining high purity epoxides (1a), however, the crystallization step is preferably performed while causing flow with a power rate required for stirring per unit volume of, for example, not less than about 0.1 kW/m$^3$, preferably not less than about 0.3 kW/m$^3$, more preferably not less than about 0.5 kW/m$^3$.

The epoxide concentration in the crystallization step is not limited to any particular level. Generally, however, said concentration is at most such that the fluidity is maintained at the end of the crystallization step. Said step can suitably be performed, for example, at an epoxide (1a) to solution ratio of not more than about 20% (w/v), preferably not more than about 10% (w/v).

The rate of crystallization is not critical. For attaining the effect of the present invention to a maximum and recovering high quality crystals, however, it is recommended that said rate be controlled such that not more than 25%, preferably not more than 10%, more preferably not more than 5%, of the whole amount of crystals obtainable crystallize out per 15 minutes.

By employing the recovery method of the present invention, it is possible to remove various impurities coexisting with the epoxides (1a), in particular threo-epoxides (3a) and dehalogenation products (5a), and at the same time obtain crystals excellent in appearance, filterability and other physical properties. Said method is thus a very simple and efficient method of recovery.

Therefore, it goes without saying that the recovery method of the present invention can be applied to the purification of epoxides (1a) by recrystallization.

In that case, the recrystallization can be effected, like the case mentioned hereinabove, by cooling to thereby reduce the solubility (crystallization upon cooling), concentrating to thereby reduce the amount remaining dissolved (crystallization upon concentration), increasing the proportion of water to thereby reduce the solubility, or a combination of these.

The water/aprotic polar organic solvent ratio in the step of recrystallization is not critical but, when expressed in terms of volume ratio at the end of the crystallization process, it may suitably be, for example, not less than about 0.1, preferably not less than about 0.3, more preferably not less than about 1. The water/aprotic polar organic solvent ratio which is preferred may vary depending on various factors, for example the aprotic polar organic solvent employed and the crystallization temperature, hence cannot be specified in all cases but can be easily determined by a simple experiment.

Although the crystallization temperature is not critical, the crystallization can suitably be effected at a low temperature at which the mixture will not solidify to about 60° C. The yield may be increased by finally cooling the mixture but, when the crystallization step is conducted at a temperature of about 0° C. to 30° C., high yields can advantageously be obtained without using any particular cryogenic apparatus.

The intensity of stirring in the recrystallization step is not critical. For obtaining high purity epoxides (1a), however, the crystallization step is preferably performed while causing flow with a power rate required for stirring per unit volume of, for example, not less than about 0.1 kW/m$^3$, preferably not less than about 0.3 kW/m$^3$, more preferably not less than about 0.5 kW/m$^3$.

The epoxide concentration in the recrystallization step is not limited to any particular level. Generally, however, said concentration is at most such that the fluidity is maintained at the end of the recrystallization step. Said step can be suitably performed, for example, at an epoxide (1a) to solution ratio of not more than about 20% (w/v), preferably not more than about 10% (w/v).

The rate of crystallization is not critical. For recovering high quality crystals, however, it is recommended that said rate be controlled such that not more than 25%, preferably not more than 10%, more preferably not more than 5%, of the whole amount of crystals obtainable crystallize out per 15 minutes.

The thus-produced (2S,3S)-1,2-epoxy-3-amino-4-phenylbutane derivatives (1a) (epoxides 1a) can be separated by a conventional solid-liquid separation technique and, optionally after washing of the cake, dried. As said solid-liquid separation technique, such conventional techniques as filtration under pressure, filtration under reduced pressure and centrifugation may be used. As regards the drying technique, drying at ordinary pressure or drying under reduced pressure (drying under vacuum) can be employed. For improving the physical and handling properties of wet crystals, the wet crystals may be subjected to washing or solvent substitution using a desired solvent.

As a preferred fundamental mode of practice of the present invention, a process for obtaining (2S,3S)-1,2-epoxy-3-N-(tert-butoxycarbonylamino)-4-phenylbutane as the epoxide (1) using (2S,3S)1-chloro-2-hydroxy-3-N-(tert-butoxycarbonyl) amino-4-phenylbutane as the starting halohydrin (2a) is described in the following.

A reaction vessel is charged with 200 g (on the pure substance basis) of (2S,3S)1-chloro-2-hydroxy-3-N-(tert-butoxycarbonyl)amino-4-phenylbutane [(3S)-2-hydroxy-3-N-(tert-butoxycarbonyl)amino-4-phenylbutane content 2.5 area percent, (2R,3S)1-chloro-2-hydroxy-3-N-(tert-butoxycarbonyl) amino-4-phenylbutane content 1.0 area percent], 1,600 ml of acetone is added, and stirring is started (stirring intensity 0.3 to 0.5 kW/m$^3$). While maintaining the inside temperature at 25° C., 400 ml (1.5 equivalents) of 10% (wt) aqueous solution of sodium hydroxide is added over 5 minutes. Three hours of stirring at a temperature of 25° C. results in the formation of (2S,3S)-1,2-epoxy-3-N-(tert-butoxycarbonyl)amino4-phenylbutane with a yield of not less than 99 mole percent. An impurity corresponding to the epoxy ring opening product (4a) is not formed at all. After stopping the stirring and the subsequent 5 minutes of standing, the aqueous layer is separated and discarded. To the organic layer remaining in the vessel, 2,400 ml of water is added over 10 hours with stirring (stirring intensity 0.3 to 0.5 kW/m$^3$) while maintaining the inside temperature at 25° C. The inside temperature is then lowered to 5° C. over 2 hours. The resulting crystals are subjected to filtration under pressure [gauge pressure 1 kg/cm$^2$, filter area about 200 cm$^2$ (filter: filter paper)], whereby crystals can be recovered in about 2 minutes. The crystals obtained are washed with 930 ml of a mixed solvent composed of acetone/water=1/3 (v/v), followed by substitution washing with 470 ml of water. The wet crystals obtained are dried under reduced pressure (1 to 30 mm Hg, 20° C. to 40° C., 10 hours), whereby at least 167 g (yield: 95 mole percent) of (2S,3S)-1,2-epoxy-3-N-(tert-butoxycarbonyl)amino-4-phenylbutane crystals are obtained.

The thus-obtained (2S,3S)-1,2-epoxy-3-N-(tert-butoxycarbonyl)amino-4-phenylbutane crystals have the following quality characteristics: appearance—snow white; content—not less than 99.5% by weight (not less than 99.5 area percent); (2R,3S)-1,2-epoxy-3-N-(tert-butoxycarbonyl) amino-4-phenylbutane content—not more than 0.1 area percent; (3S)-2-hydroxy-3-N-(tert-butoxycarbonyl)amino-4-phenylbutane content—not more than 0.1 area percent.

Thus, according to the present invention, high quality epoxides (1a) can be produced efficiently in a very simple manner and the yield from halohydrins (2a) can be expected to amount to not less than 90 mole percent, preferably not less than 95 mole percent. Further purification is not necessary.

BEST MODE FOR CARRYING OUT THE INVENTION

The following examples and reference examples are further illustrative of the present invention but are by no means limitative of the scope of the present invention.

Example 1

The (2S,3S)1-chloro-2-hydroxy-3-(N-tert-butoxycarbonyl)amino-4-phenylbutane prepared in Reference Example 1 was used in an amount of 2.00 g on the pure substance basis. To this was added 16 ml of acetone and 4 ml of 10% (wt) aqueous sodium hydroxide solution, and the mixture was stirred at 30° C. for 2 hours. After allowing the mixture to stand, the aqueous layer was separated and discarded, whereby an acetone solution containing a small amount of water was obtained. This acetone solution contained 1.74 g (yield: 99 mole percent) of (2S,3S)-1,2-epoxy-3-N-(tert-butoxycarbonyl)amino-4-phenylbutane. There was observed no epoxy ring opening product (4a) formation.

To this acetone layer was added 24 ml of water over 10 hours at an inside temperature of 25° C. The mixture was then cooled to 5° C. The resulting crystalline precipitate was separated by filtration under reduced pressure [filter area 3 cm$^2$; filter: filter paper (1 micron)]. About 30 seconds was required for the filtration. After washing with 10 ml of a mixed solvent composed of acetone/water=1/3 (v/v), substitution washing was performed with 5 ml of water. Drying under vacuum gave 1.71 g of snow white crystals of (2S,3S)-1,2-epoxy-3-N-(tert-butoxycarbonyl)amino-4-phenylbutane (purity 99.7 area percent, yield 97 mole percent). The impurities contained in the crystals were as follows: (2R,3S)-1,2-epoxy-3-N-(tert-butoxycarbonyl) amino-4-phenylbutane (content less than 0.1 area percent), (3S)-2-hydroxy-3-N-(tert-butoxycarbonyl)amino-4-phenylbutane (content 0.1 area percent).

Example 2

(2S,3S)1-Chloro-2-hydroxy-3-(N-tert-butoxycarbonyl)amino-4-phenylbutane [(3S)-2-hydroxy-3-N-(tert-butoxycarbonyl)amino-4-phenylbutane content 1.4 area percent, (2R,3S)1-chloro-2-hydroxy-3-N-(tert-butoxycarbonyl)amino-4-phenylbutane content 1.0 area percent] prepared in the same manner as in Reference Example 1 was used in an amount of 2.00 g on the pure substance basis. To this was added 16 ml of acetone and 4 ml of 10% (wt) aqueous sodium hydroxide solution, and the mixture was stirred at 30° C. for 2 hours. After allowing the mixture to stand, the aqueous layer was separated and discarded, whereby an acetone solution containing a small amount of water was obtained. This acetone layer contained 1.75 g (yield: 100 mole percent) of (2S,3S)-1,2-epoxy-3-N-(tert-butoxycarbonyl)amino-4-phenylbutane. There was observed no epoxy ring opening product (4a) formation.

To this acetone layer was added 7 ml of water over 1 hour at an inside temperature of 25° C. The mixture was then cooled to 5° C. The resulting crystalline precipitate was collected by filtration and washed with 10 ml of a mixed solvent composed of acetone/water=1/3 (v/v), followed by substitution washing with 5 ml of water. Drying under vacuum gave 1.62 g of snow white crystals of (2S,3S)-1,2-epoxy-3-N-(tert-butoxy carbonyl)amino-4-phenylbutane (purity 99.7 area percent, yield 92 mole percent). The impurities contained in said crystals were as follows: (2R, 3S)-1,2-epoxy-3-N-(tert-butoxycarbonyl)amino-4-phenylbutane (content less than 0.1 area percent), (3S)-2-hydroxy-3-N-(tert-butoxycarbonyl)amino-4-phenylbutane (content 0.1 area percent).

Example 3

(2S, 3S)1-Chloro-2-hydroxy-3-(N-tert-butoxycarbonyl)amino-4-phenylbutane [(3S)-2-hydroxy-3-N-(tert-butoxycarbonyl)amino-4-phenylbutane content 2.2 area percent, (2R,3S)1-chloro-2-hydroxy-3-N-(tert-butoxycarbonyl)amino-4-phenylbutane content 1.0 area percent] prepared in the same manner as in Reference Example 1 was used in an amount of 2.00 g on the pure substance basis. To this was added 16 ml of acetone and 4 ml of 10% (wt) aqueous sodium hydroxide solution, and the mixture was stirred at 25° C. for 2 hours. After allowing the mixture to stand, the aqueous layer was separated and discarded out of the system, whereby an acetone solution containing a small amount of water was obtained. This acetone layer contained 1.75 g (yield: 100 mole percent) of (2S,3S)-1,2-epoxy-3-N-(tert-butoxycarbonyl)amino-4-phenylbutane. There was observed no epoxy ring opening product (4a) formation.

To this acetone layer was added 24 ml of water over hour at an inside temperature of 25° C. The resulting crystalline precipitate was collected by filtration and washed with 10 ml of a mixed solvent composed of acetone/water=1/3 (v/v), followed by substitution washing with 5 ml of water. Drying under vacuum gave 1.69 g of snow white crystals of (2S,3S)-1,2-epoxy-3-N-(tert-butoxycarbonyl) amino-4-phenylbutane (purity 99.7 area percent, yield 96 mole percent). The impurities contained in said crystals were as follows: (2R,3S)-1,2-epoxy-3-N-(tert-butoxycarbonyl) amino-4-phenylbutane (content less than 0.1 area percent), (3S)-2-hydroxy-3-N-(tert-butoxycarbonyl)amino-4-phenylbutane (content 0.1 area percent).

Example 4

(2S,3S)1-Chloro-2-hydroxy-3-(N-tert-butoxycarbonyl)-amino-4-phenylbutane [(3S)-2-hydroxy-3-N-(tert-butoxycarbonyl)-amino-4-phenylbutane content 2.2 area percent, (2R,3S)1-chloro-2-hydroxy-3(S)-N-(tert-butoxycarbonyl)-amino4-phenylbutane content 1.0 area percent] prepared in the same manner as in Reference Example 1 was used in an amount of 2.00 g on the pure substance basis. To this was added 20 ml of acetone and 800 mg of sodium hydroxide powder, and the mixture was stirred at 25° C. for 2 hours, whereby (2S,3S)-1,2-epoxy-3-N-(tert-butoxycarbonyl)amino-4-phenylbutane was formed in almost quantitative yield. There was observed no epoxy ring opening product (4a) formation. The insoluble matter (sodium hydroxide and sodium chloride) was removed by filtration, 32 ml of water was added over 10 hours, and the resulting crystalline precipitate was collected by filtration and washed with 10 ml of a mixed solvent composed of acetone/water=1/3 (v/v), followed by substitution washing with 5 ml of water. Drying under vacuum gave 1.64 g of snow white crystals of (2S,3S)-1,2-epoxy-3-N-(tert-butoxycarbonyl) -amino-4-phenylbutane (purity 99.7 area percent, yield 93 mole percent). The impurities contained in said crystals were as follows: (2R,3S)-1,2-epoxy-3-N-(tert-butoxycarbonyl)amino-4-phenylbutane phenylbutane (content less than 0.1 area percent), (3S)-2-hydroxy-3-N-(tert-butoxycarbonyl)amino-4-phenylbutane (content 0.1 area percent).

Example 5

(2S,3S)1-Chloro-2-hydroxy-3-(N-tert-butoxycarbonyl)-amino-4-phenylbutane [(3S)-2-hydroxy-3-N-(tert-butoxycarbonyl)-amino-4-phenylbutane content 2.6 area percent, (2R,3S)1-chloro-2-hydroxy-3(S)-N-(tert-butoxycarbonyl)-amino4-phenylbutane content 1.0 area percent] prepared in the same manner as in Reference Example 1 was used in an amount of 2.00 g on the pure substance basis. To this was added 16 ml of acetonitrile and 4 ml of aqueous sodium hydroxide solution (1.5 equivalents), and the mixture was stirred at room temperature for 2 hours. After allowing the mixture to stand, the aqueous layer was separated and discarded, whereby an acetonitrile solution containing a small amount of water was obtained. This acetonitrile layer contained 1.75 g of (2S,3S)-1,2-epoxy-3-N-(tert-butoxycarbonyl)amino-4-phenylbutane (yield 100 mole percent). There was observed no epoxy ring opening product (4a) formation. To this acetonitrile layer was added 24 ml of water over 1 hour. The resulting crystalline precipitate was collected by filtration and washed with an ample amount of water. Drying under vacuum gave 1.60 g of snow white crystals of (2S,3S)-1,2-epoxy-3-N-(tert-butoxycarbonyl)amino-4-phenylbutane (purity 99.7 area percent, yield 91 mole percent). The impurities contained in said crystals were as follows: (2R,3S)-1,2-epoxy-3-N-(tert-butoxycarbonyl)amino-4-phenylbutane (content less than 0.1 area percent), (3S)-2-hydroxy-3-N-(tert-butoxycarbonyl)-amino-4-phenylbutane (content 0.1 area percent).

Example 6

(2S,3S)-1,2-Epoxy-3-N-(tert-butoxycarbonyl)amino-4-phenylbutane phenylbutane [(3S)-2-hydroxy-3-N-(tert-butoxycarbonyl)amino-4-phenylbutane content 2.2 area percent, (2R,3S)-1,2-epoxy-3-N-(tert-butoxycarbonyl)amino-4-phenylbutane content 1.0 area percent] was used in an amount of 10.0 g on the pure substance basis. To this was added 80 ml of acetone for complete dissolution. To this acetone solution was added 120 ml of water over 10 hours with stirring (stirring intensity 0.3 to 0.5 kw/m$^3$) while the temperature was maintained at 25° C. followed by cooling to 5° C. The resulting crystalline precipitate was collected by filtration and washed with 50 ml of a mixed solvent composed of acetone/water=1/3 (v/v), followed by substitution washing with 25 ml of water. Drying under vacuum gave 9.8 g of snow white crystals of (2S,3S)-1,2-epoxy-3-N-(tert-butoxycarbonyl)amino-4-phenylbutane (purity 99.7 area percent, yield 98 mole percent). The impurities contained in said crystals were as follows: (2R,3S)-1,2-epoxy-3-N-(tert-butoxycarbonyl)amino-4-phenylbutane (content less than 0.1 area percent), (3S)-2-hydroxy-3-N-(tert-butoxycarbonyl)-amino-4-phenylbutane (content 0.1 area percent).

Example 7

(2S,3S)1-Chloro-2-hydroxy-3-N-(isopropoxycarbonyl)-amino4-phenylbutane [(3S)-2-hydroxy-3-N-(isopropoxycarbonyl)-amino4-phenylbutane content 1.0 area percent, (2R,3S)1-chloro-2-hydroxy-3-N-(isopropoxycarbonyl)amino-4-phenylbutane content 1.0 area percent], prepared in the same manner as in Reference Example 1 except that (3S)1-chloro-2-oxo-3-N-(isopropoxycarbonyl)amino-4-phenylbutane was used in lieu of (3S)1-chloro-2-oxo-3-N-(tert-butoxycarbonyl)amino-4-phenylbutane, was used in an amount of 8.89 g on the pure substance basis. To this was added 70 ml of acetone and 15 ml of 10% (wt) aqueous sodium hydroxide solution, and the mixture was stirred at 25° C. for 1 hour. After allowing the mixture to stand, the aqueous layer was separated and discarded, whereby an acetone solution containing a small amount of water was obtained. There was observed no epoxy ring opening product (4a) formation.

To this acetone layer was added 140 ml of water over 1 hour at an inside temperature of 25° C. The mixture was then cooled to 5° C. The resulting crystalline precipitate was collected by filtration under reduced pressure and washed with a mixed solvent composed of acetone/water=1/3 (v/v), followed by drying under vacuum, which gave 7.11 g of snow white crystals of (2S,3S)-1,2-epoxy-3-N-(tert-butoxycarbonyl) amino-4-phenylbutane (purity 99.8 area percent, yield 92 mole percent). The impurities contained in said crystals were as follows: (2R,3S)-1,2-epoxy-3-N-

(isopropoxycarbonyl)amino-4-phenylbutane (content 0.1 area percent), (3S)-2-hydroxy-3-N-(isopropoxycarbonyl) amino-4-phenylbutane (content 0.1 area percent).

Example 8

The process of the present invention is applicable also to the synthesis of epoxides derived from amino acids other than phenylalanine. For example, (2S,3R)-1,2-epoxy-3-N-(benzyloxycarbonyl)amino-4-phenylthiobutane can be synthesized by treating (2S,3R)1-chloro-2-hydroxy-3-N-(benzyloxycarbonyl)amino-4-phenylthiobutane (synthesizable from serine according to the process of WO 95/09843) with a base in an aprotic polar organic solvent or a mixed solvent composed of an aprotic polar organic solvent and water, without formation, as a byproduct, of (2S,3R)1-alkoxy-2-hydroxy-3-N-(benzyloxycarbonyl) amino-4-phenylthiobutane, which corresponds to the epoxy ring opening product (4a).

To 18.3 g (on the pure substance basis) of (2S,3R)1-chloro-2-hydroxy-3-N-(benzyloxycarbonyl)amino-4-phenylthiobutane was added 120 ml of acetone and 30 ml of 10% (wt) aqueous sodium hydroxide solution, and the mixture was stirred at 30° C. for 2 hours. After allowing the mixture to stand, the aqueous layer was separated and discarded, whereby an acetone solution containing a small amount of water was obtained. In the acetone layer, there was confirmed formation, in almost quantitative yield, of (2S,3R)-1,2-epoxy-3-N-(benzyloxycarbonyl)amino-4-phenylthiobutane. Formation of (2S,3R)1-alkoxy-2-hydroxy-3-N-(benzyloxycarbonyl) amino-4-phenylthiobutane, which corresponds to the epoxy ring opening product (4a), was not detected.

Reference Example 1

Production of (2S,3S)1-chloro-2-hydroxy-3-(N-tert-butoxycarbonyl)amino-4-phenylbutane THF (25 ml) and 100 ml of ethanol were added to 25 g of (3S)1-chloro-2-oxo-3-N-(tert-butoxycarbonyl)amino-4-phenylbutane, and the mixture was cooled to 10° C. To this solution was added a solution composed of 1.59 g of sodium borohydride, 25 ml of ethanol and 25 ml of THF. The mixture was stirred at 10° C. to 20° C. for 1 hour. While maintaining the inside temperature at 10° C. to 15° C., 125 ml of 1.6% (wt) aqueous sulfuric acid solution was added and the pH was adjusted to 6.5 with 30% (wt) aqueous sodium hydroxide solution. The temperature was then raised to 50° C. and, after 1 hour of stirring, the mixture was cooled to 5° C. and stirring was continued for 1 hour. The resulting crystals were collected by filtration and subjected to washing under revolving with four portions of 300-mL of a mixed solvent composed of THF/water=1/4 (v/v), two portions of 70-ml of cold ethanol and two portions of 180-mL of water. Drying under vacuum gave 14.6 g of (2S,3S)1-chloro-2-hydroxy-3-(N-tert-butoxycarbonyl)amino-4-phenylbutane as crystals (purity 95.9%, yield 56%). The crystals obtained contained, as the major impurity, 2.6 area percent of (3S)-2-hydroxy-3-N-(tert-butoxycarbonyl)amino-4-phenylbutane and, as the next major impurity, 1.0 area percent of (2R,3S)1-chloro-2-hydroxy-3-(S)-N-(tert-butoxycarbonyl)amino-4-phenylbutane.

Comparative Example

Production of (2S,3S)-1,2-epoxy-3-N-(tert-butoxycarbonyl)-amino-4-phenylbutane according to the technology of WO 96/17821

The (2S,3S)-1-chloro-2-hydroxy-3-(N-tert-butoxycarbonyl)-amino-4-phenylbutane prepared in Reference Example 1 was used in an amount of 2.00 g on the pure substance basis. To this was added 11 ml of THF, and the mixture was cooled to 5 ° C. Thereto was added over 15 minutes a solution composed of 1.49 g of potassium hydroxide and 5.9 ml of methanol while maintaining the inside temperature at 5° C. to 8° C. The mixture was then stirred at 20° C. to 22° C. for 75 minutes, whereupon the starting material was found to have disappeared and (2S,3S)-1,2-epoxy-3-N-(tert-butoxycarbonyl)amino-4-phenylbutane formed in 87 mole percent yield. (2S,3S)1-Methoxy-2-hydroxy-3-N-(tert-butoxycarbonyl)amino-4-phenylbutane, which is the byproduct epoxy ring opening product, was found to occur in an amount of 11 area percent. This reaction mixture was added to 67 ml of water over 10 minutes and the whole mixture was stirred for 1 hour. The resulting crystalline precipitate was collected under reduced pressure [filter area 3 cm$^2$; filter: filter paper (1 micron)] in the same manner as in Example 1. This filtration required about 5 minutes; poor filterability was thus suggested. Washing with 67 ml of water and drying under vacuum gave 1.63 g of crystals of (2S,3S)-1,2-epoxy-3-N-(tert-butoxycarbonyl) amino-4-phenylbutane (purity 92.5 area percent, yield 86 mole percent (the yield of crystals as obtained was 93 mole percent)). The crystals obtained were found slightly colored as compared with the crystals obtained in Examples 1 to 6. The crystals contained the following impurities: (2S,3S)-1-methoxy-2-hydroxy-3-N-(tert-butoxycarbonyl)amino-4-phenylbutane (content 5.3 area percent), (3S)-2-hydroxy-3-N-(tert-butoxycarbonyl)amino-4-phenylbutane (content 1.3 area percent), (2R,3S)-1,2-epoxy-3-N-(tert-butoxycarbonyl) amino-4-phenylbutane (content 0.5 area percent).

We claim:

1. A process for producing 1,2-epoxy-3-amino-4phenylbutane derivatives of the formula (1)

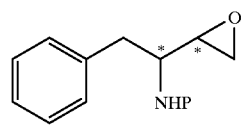

(1)

(wherein P is an amino-protecting group of the urethane type and the configurations at positions 2 and 3 are collectively 2S,3S or 2R,3R), which comprises treating a 1-halo-2-hydroxy3-amino-4-phenylbutane derivative of the formula (2)

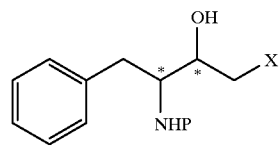

(2)

(wherein X is a halogen atom, P is as defined above and the configurations at positions 2 and 3 are such that when, in formula (1), the configurations at positions 2 and 3 are collectively 2S,3S, they are collectively 2S,3S and, when the configurations in formula (1) are collectively 2R,3R, they are collectively 2R,3R), with a base in an aprotic polar organic solvent or a mixed solvent consisting essentially of an aprotic polar organic solvent and water and then causing the resulting 1,2-epoxy-3-amino-4-phenylbutane derivative (1) to crystallize out from a mixed solvent consisting essentially of an aprotic polar organic solvent and water.

2. The process according to claim 1, wherein the 1,2-epoxy-3-amino-4-phenylbutane derivative of formula (1) is produced with the 1-halo-2-hydroxy-3-amino-4-phenylbutane derivative of formula (2) containing, as an impurity, a threo1-halo-2-hydroxy-3-amino-4-phenylbutane derivative of the formula (6)

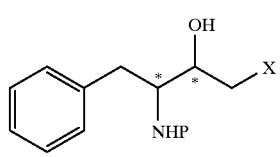

(6)

(in which P is as defined above and the configurations at positions 2 and 3 are such that when, in formula (1), the configurations at positions 2 and 3 are collectively 2S,3S, they are collectively 2R,3S and, when the configurations in formula (1) are collectively 2R,3R, they are collectively 2S,3R), or a 2-hydroxy-3-amino-4-phenylbutane derivative of the formula (5)

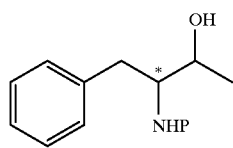

(5)

(in which P is as defined above and the configuration at position 3 is 3S when, in formula (1), the configurations at positions 2 and 3 are collectively 2S,3S, or 3R when the configurations in formula (1) are collectively 2R,3R), without formation, as a byproduct, of an 1-alkoxy-2-hydroxy-3-amino-4-phenylbutane derivative of the formula (4)

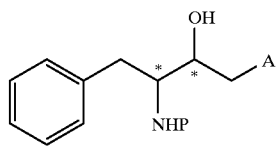

(4)

(in which P is as defined above and the the configurations at positions 2 and 3 are such that when, in formula (1), the configurations at positions 2 and 3 are collectively 2S,3S, they are collectively 2S,3S and, when the configurations in formula (1) are collectively 2R,3R, they are collectively 2R,3R), and then an impurity coexisting with the resulting 1,2-epoxy-3-amino-4-phenylbutane derivative of formula (1), namely a threo-1,2-epoxy-3-amino-4-phenylbutane derivative of the formula (3)

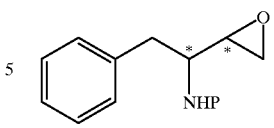

(3)

(in which P is as defined above and the the configurations at positions 2 and 3 are such that when, in formula (1), the configurations at positions 2 and 3 are collectively 2S,3S, they are collectively 2R,3S and, when the configurations in formula (1) are collectively 2R,3R, they are collectively 2S,3R), or the 2-hydroxy-3-amino-4-phenylbutane derivative of formula (5) is removed.

3. The process according to claim 1, wherein the aprotic polar organic solvent is acetone, acetonitrile or THF.

4. The process according to claim 1, wherein the water/aprotic polar organic solvent ratio in the crystallization step is not less than 0.1 at the end of said step.

5. The process according to claim 1, wherein, in formulas (1), (2), (3), (4), (5) and (6), the amino-protecting group on the amino group at position 3 is benzyloxycarbonyl, methoxycarbonyl or tert-butoxycarbonyl.

6. The process according to claim 1, wherein, in formulas (2) and (6), the halogen atom at position 1 is a chlorine or bromine atom.

7. The process according to claim 1, wherein the base is an alkali metal hydroxide, an alkali metal carbonate, an alkaline earth metal hydroxide or an alkaline earth metal carbonate.

8. The process according to claim 1, wherein the base component in the system is annihilated or removed prior to the crystallization step.

9. The process according to claim 1, wherein the intensity of stirring in the crystallization step is not less than 0.1 kW/m$^3$.

10. The process according to claim 1, wherein, in the crystallization step, the product (1) crystallizes out at a rate such that not more than 25% of the whole amount of crystals that are obtainable crystallize out per 15 minutes.

11. A method of recovering 1,2-epoxy-3-amino-4phenylbutane derivatives of the formula (1)

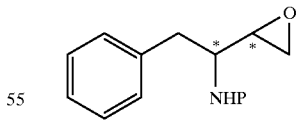

(1)

(wherein P is an amino-protecting group of the urethane type and the configurations at positions 2 and 3 are collectively 2S,3S or 2R,3R), which comprises causing an 1,2-epoxy-3-amino4-phenylbutane derivative of formula (1) to crystallize out from a mixed solvent composed of an aprotic polar organic solvent and water.

12. The method according to claim 11, wherein a threo-1,2-epoxy-3-amino-4-phenylbutane derivative of the formula (3)

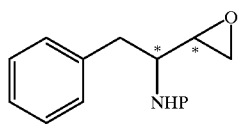

(3)

(in which P is as defined above and the the configurations at positions 2 and 3 are such that when, in formula (1), the configurations at positions 2 and 3 are collectively 2S,3S, they are collectively 2R,3S and, when the configurations in formula (1) are collectively 2R,3R, they are collectively 2S,3R), or a 2-hydroxy-3-amino-4-phenylbutane derivative of the formula (5)

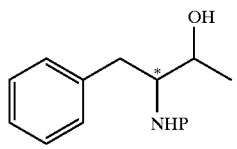

(5)

(in which P is as defined above and the configuration at position 3 is 3S when, in formula (1), the configurations at positions 2 and 3 are collectively 2S,3S, or 3R when the configurations in formula (1) are collectively 2R,3R), each existing as an impurity is removed.

13. The method according to claim 11, wherein the aprotic polar organic solvent is acetone, acetonitrile or THF.

14. The method according to claim 11, wherein the water/aprotic polar organic solvent ratio in the crystallization step is not less than 0.1 at the end of said step.

15. The method according to claim 11, wherein, in formulas (1), (3) and (5), the amino-protecting group on the amino group at position 3 is benzyloxycarbonyl, methoxycarbonyl or tert-butoxycarbonyl.

16. The method according to claim 11, wherein the intensity of stirring in the crystallization step is not less than 0.1 kW/m$^3$.

17. The method according to claim 11, wherein, in the crystallization step, the product (1) crystallizes out at a rate such that not more than 25% of the whole amount of crystals that are obtainable crystallize out per 15 minutes.

18. The process according to claim 2, wherein the aprotic polar organic solvent is acetone, acetonitrile or THF.

19. The process according to claim 2. wherein the water/aprotic polar organic solvent ratio in the crystallization step is not less than 0.1 at the end of said step.

20. The process according to claim 3, wherein the water/aprotic polar organic solvent ratio in the crystallization step is not less than 0.1 at the end of said step.

* * * * *

UNITED STATES PATENT AND TRADEMARK OFFICE
CERTIFICATE OF CORRECTION

PATENT NO. : 5,936,104
DATED : Aug. 10, 1999
INVENTOR(S): Nishiyama et al

It is certified that error appears in the above-identified patent and that said Letters Patent is hereby corrected as shown below:

Title page, Item [75] Inventors: The residence of the last-named inventor should read ---Matsubara---.

Signed and Sealed this

Twenty-first Day of December, 1999

Attest:

Q. TODD DICKINSON

*Attesting Officer*    *Acting Commissioner of Patents and Trademarks*